| United States Patent [19] | [11] Patent Number: 4,916,161 |
| --- | --- |
| Patell | [45] Date of Patent: Apr. 10, 1990 |

[54] TASTE-MASKING PHARMACEUTICAL AGENTS

[75] Inventor: Mahesh K. Patell, Edison, N.J.

[73] Assignee: Bristol-Myers Squibb, New York, N.Y.

[21] Appl. No.: 262,911

[22] Filed: Oct. 25, 1988

[51] Int. Cl.⁴ .................... A61K 9/62; B01J 13/02; B05D 7/00; B22B 9/02

[52] U.S. Cl. ................................... 514/570; 514/781; 514/974; 427/3

[58] Field of Search ............... 514/570, 781, 974; 427/3

[56] References Cited

U.S. PATENT DOCUMENTS 4,460,563  7/1984  Calanchi ........................... 424/494

Primary Examiner—John Kight
Assistant Examiner—Nathan M. Nutter
Attorney, Agent, or Firm—Sandra M. Nolan

[57] ABSTRACT

The unpleasant taste of ibuprofen or other bad-tasting pharmaceuticals can be mediated via wet granulation using certain taste masking agents.

13 Claims, No Drawings

TASTE-MASKING PHARMACEUTICAL AGENTS

This invention relates to a process for taste masking ibuprofen or other unpleasant tasting substances. More particularly, it concerns a process for wet granulating a mixture of ibuprofen, and hydroxypropyl methylcellulose phthalate (hereinafter sometimes referred to as HPMCP) with an aqueous composition in which the HPMCP is at least partly soluble to affect an improvement in the taste of ibuprofen.

The unpleasant taste of ibuprofen is well documented in the prior art and the efforts to overcome this bad taste have been numerous. One such effort involves converting the ibuprofen to an aluminum salt and U.S. Pat. No. 4,361,580 is exemplary of such efforts.

Other suggested procedures for masking the taste of ibuprofen involve the preparation of derivatives of ibuprofen that do not have its unpleasant taste. U.S. Pat. No. 4,049,700 prepares ibuprofen p-hydroxyphenylurea ester while U.S. Pat. No. 4,049,699 provides ibuprofen p-hydroxybenzaldehyde semicarbazone ester for the same purpose.

Still other procedures taught in the prior art suggest coating finished tablets of ibuprofen with taste-masking water insoluble ethylcellulose. U.S. Pat. No. 4,693,896 is an example of this kind of procedure. Another method is disclosed in Japanese Patent No. 81/46,837 which suggests coating particles of ibuprofen with β-cyclodextrin (i.e., beta-cyclodextrin). See *Chemical Abstracts* Vol. 95, (1981) page 382, 95:156580m. However, B-Cyclodextrin is not approved for internal use in the United States. It is only allowed for internal use in Japan and Eastern European countries. Also, B-cyclodextrin is very expensive and is known to interfere with, and modify, the bioavailability of drugs due to its property to form complex with the drug molecule.

Hydroxypropylmethyl cellulose phthalate has been widely used in the United States, in Japan and in European countries as an enteric coating polymer. It is listed in the National Formulary (NF) making it an official compendium material. It is relatively inexpensive compared with B-cyclodextrin, commercially available and widely used in the food and pharmaceutical industries.

It has now been found that a highly satisfactory ibuprofen product, in which the bad taste of the ibuprofen is effectively masked, can be made by wet granulating the combination of ibuprofen and HPMCP with an aqueous granulating composition in which the HPMCP is at least partially soluble. Since the HPMCP is not soluble in pure water, it is necessary to adjust the pH of the aqueous granulating composition with an alkalizing agent or a buffering system so that it has a pH of 5.5 or higher. The ibuprofen granulations prepared in this fashion may be used as such, or they may be compressed into tablets, as described in more detail below.

The concepts of wet granulating and the granulations prepared by such a process are well known to those skilled in the pharmaceutical arts. In a wet granulating process, the material to be granulated, usually in powdered form, it wetted with an aqueous composition of a granulating agent to cause the powdered material to agglomerate. This agglomerated product is subsequently dried and then generally ground to reduce the size of the agglomerates to a size that is suitable for use. Usually, this type of process is used to form tablets of the material.

The granulation particles prepared by such a process are quite distinct from granules obtained merely by grinding larger pieces of a material to reduce its particle size. For instance, the granulations prepared by this process are devoid of the unpleasant taste of ibuprofen, probably due to the coating of Hydroxypropyl methylcellulose phthalate which becomes partially soluble in presence of alkalizing agents.

The HPMCP used as the taste masking agent in the present invention is derived from hydroxypropyl methylcellulose by esterification with phthalic anhydride. HPMCP is sold commercially by Shin-Etsu Chemical and is described in detail in its publication entitled "Hydroxypropyl Methylcellulose Phthalate, Technical Bulletin of HPMCP Appendix-2" Biddle Sawyer Corporation, New York, N.Y., which publication is incorporated herein by reference.

As is clear from this publication, the HPMCP is available in at least two grades, i.e. HP-50 and HP-55, which differ a little from each other in the analysis of the substituent groups on the cellulose backbone, i.e. free phthalic acid, carboxybenzoil groups, methoxy groups and hydroxypropyl group. Either of these grades of HPMCP may be used in the practice of this invention. HPMCP is also available commercially under the trademark SD EUDRAGIT L100.

In making the granulations of the present invention, it has been found to be effective to first prepare a dry pregranulation blend containing the ibuprofen and HPMCP. The granulating solution is then added to this pre-granulation blend to form the granulation which is further processed to obtain the granulation in suitable form and size for use as such as a dosage form or as one component of a composite dosage form. The quantity of ibuprofen that may be contained in said pre-granulation blend may vary somewhat. However, generally it will comprise from about 10% to about 50% by weight of said pregranulation blend based on the total weight of said blend and preferably from about 30% to about 40% by weight on the same weight basis.

Similarly, the quantity of HPMCP that may be contained in the pre-granulation blend may also vary somewhat. In the usual cases the HPMCP will constitute from about 5% to about 15% by weight of the pre-granulation blend based on the total weight of the pre-granulation blend. In the preferred cases, the HPMCP will comprise about 8% to about 10% of the pre-granulation blend on the same weight basis.

In addition to the ibuprofen and HPMCP, the pre-granulation blend may also contain a variety of adjuvants commonly added to pre-granulation blends of this character. Thus, suitable quantities of such agents as sugars, Dextrose, Sorbitol and mannitol; bulking agents, such as Microcrystalline Cellulose, and starch and the like can be used Other conventional excipients can be employed.

The granulating composition used in this invention is an aqueous composition in which the HPMCP is at least partially soluble. HPMCP is insoluble in pure water and consequently pure water is not suitable as a granulating composition. HPMCP, however, is soluble in aqueous alkaline solutions or solutions that are buffered at a pH of about 5, preferably about 5.5 or greater. Aqueous acid solutions, even though they have a pH of about 5 will not adequately dissolve HPMCP and consequently cannot bee employed as granulating solution.

In general terms, it may be said that the granulating compositions that may be utilized in the present invention are aqueous compositions selected from the group consisting of aqueous alkaline solutions and aqueous solutions containing one or more buffering systems that buffer the pH of the aqueous solution at a pH of 5 or greater. The upper pH range of the granulating composition used in the present invention does not appear to be a critical feature. However, as a practical matter, it generally will not exceed a pH of about 8.0.

Types of granulating compositions that has been found to be particularly advantageous in the practice of the present invention are buffered aqueous compositions prepared by dissolving an alkali metal citrate, e.g. potassium citrate, in an aqueous carrier. In this case, the concentration of the alkali metal citrate in this aqueous composition will generally be in the range of from about 50% to about 80% by weight, preferably about 60% to about 70%, based on the total weight of the aqueous granulating composition. This will generally give a pH in the range of from about 4 to about 7 and preferably in the range of from about 5 to about 6.

In addition to the alkalizing agent or buffering system the aqueous granulating composition used herein may also contain other adjuvants. These include flavoring agents, binding agents, processing and the like. Examples of such adjuvants include sweetners such as saccharin, aspartame; flavoring agents such as artifical and or natural flavors, citric and tartaric acids. Binders such as starch, povidone; flavor enhancers, such as magnasweet and prosweet. The quantities used are suitable for their function in the compositions.

In practicing the process of the present invention, a dry pre-granulation blend will be prepared by dry-blending and thoroughly mixing the desired quantity of ibuprofen, HPMCP and the desired adjuvants. The aqueous granulating composition described above is then added to the pre-granulation blend and the two are mixed until a uniform granulation is obtained. The relative quantities of pre-granulation blend and aqueous granulating composition that will be mixed together may vary. Generally, on a weight basis from about 0.05 parts to about 0.2 parts of aqueous granulating composition will be used per part of pre-granulation blend. For optimum results, this ratio is from about 0.09 parts to about 0.1 parts of aqueous granulating composition per part of pre-granulation blend.

The granulation mass prepared as described above is ground in any suitable manner and then dried. Any of a number of devices and techniques known in this art can be used to perform these steps. Thus, a Tornado Mill or similar device may be used to grind the granulation. A fluid bed dryer may be used to dry the ground granulation. Other conventional processing apparatuses and/or techniques may be employed.

The dried granulation product is then sized using any of several well known techniques. One very suitable procedure involves the use of an oscillating screen, having mesh size in the range of from 12 mesh to about 16 mesh. Similarly, sizing of the particles can be also achieved by using Tornado Mill, Fitz Mill, or quick sieve machines, and the like.

It is a feature of the present invention to use the granulation described above to prepare ibuprofen tablets in which the bad taste of the ibuprofen is masked. To this end, this granulation is blended with tablet adjuvants that are added to facilitate the manufacture of the tablet, to improve its esthetics or to improve the organoleptics of the tablet or to serve as bulking agents for the tablet. Suitable quantities of a large number of tablet adjuvants are known in this art that may be used for the present purposes. These include stablizers, colorants, fillers, and the like. Useful materials include fillers such as direct compressible sugars, Dextrose, Sorbitol, or Mannitol; compression aids e.g., microcrystalline cellulose, starch; lubricants, such as stearates; stearic acid, variety of flavors and flavor enhancers such as prosweet, magnasweet, citric acid.

The ratio of the amount of ibuprofen granulation product described above to the total amount of tablet adjuvants employed in making the present tablets may vary somewhat. Generally, on a weight basis (based on the tablet composition weight), from about 1 parts to about 3 parts of total tablet adjuvants will be mixed with about 1 part of ibuprofen granulation, with the preferred range being from about 2 parts to about 3 parts of total adjuvants to about 1 part of ibuprofen granulation product.

The final blend of ibuprofen granulation product and tablet adjuvants is fed to tablet presses in which the final tablets are formed. This is a standard procedure and is well known to those skilled in this art and need not be elaborated on here.

While the discussion herein centers on ibuprofen, it is contemplated that other foul-tasting pharmaceutical agents, e g. quaifenesin, acetaminophen; caffeine, and the like, can also be taste-masked using the invention.

The following Examples are given to further illustrate this invention. It is to be understood, however, that this invention is not limited thereto.

EXAMPLE 1

| Formula 2584 | | | |
|---|---|---|---|
| mg/tablet | Item No. | Ingredients | % w/wt. |
| Part I - Granulation | | | |
| 50.00 | 1 | Ibuprofen USP | 9.346 |
| 12.00 | 2 | Hydroxypropyl Methycellulose Phthalate HP-55F (Shin-Etsu Chemicals) NF | 2.243 |
| 30.00 | 3 | Cellulose Microcrystalline PH105 NF | 5.607 |
| 40.00 | 4 | Confectionery Sugar 6X NF | 7.477 |
|  | 5 | Water, Deionized and Distilled |  |
| 2.00 | 6 | Calcium Saccharin USP | 0.374 |
| 8.00 | 7 | Potassium citrate USP | 1.495 |
| Part II - Final Blend | | | |
| 41.00 | 8 | Mannitol Granular USP | 7.663 |
| 300.00 | 9 | Sugar Compressible (DiPac-Amstar) NF | 56.075 |
| 6.00 | 10 | Calcium Saccharin USP | 1.121 |
| 9.60 | 11 | Citric Acid Anhydrous Powder USP | 1.795 |
| 3.00 | 12 | Fruit Punch Flavor (FMC) | 0.561 |
| 5.00 | 13 | Magnasweet 180 Flavor Enhancer | 0.935 |
| 0.40 | 14 | FD & C Red #40 Lake - 15% Dye | 0.075 |
| 20.00 | 15 | Cellulose Microcrystalline PH101 NF | 3.738 |
| 8.00 | 16 | Magnesium Stearate USP | 1.495 |
| 535.00 | | | 100.000 |

PROCEDURE
Part I: Granulation

Step A: Mix items 1, 2, 3 & 4 in Hobart mixer, mix for short 5 minutes (screen each item separately if lumpy).

Step B: Dissolve items 6 and 7 in 5 (use 500 ml water per 5680 gm granulation), add to the product of Step A, complete granulation by adding 300 ml water. Mix until uniform granulation is formed.

Step C: Pass the product of Step B through Tornado Mill, dry in fluid bed dryer, inlet temp. 60° C., outlet temp. 30° C. (approx. 1.5% LOD).

Formula 2584 (continued)

| | |
|---|---|
| Step D: | Pass dried granulation of Step C through #16 screen using oscillator |

Part II: Dry Mix and Final Blend

| | |
|---|---|
| Step A: | Pass 10, 11, 12, 13, 14 and 15 through 30 mesh screen. |
| Step B: | Add mixture from Step A to small Twin Shell Blender with intensifier bar. Mix for 15 minutes using intensifier bar 3 times, 2 revolutions each time and discharge. |
| Step C: | Add to appropriate Twin Shell Blender Part I granulation, the product of Step B, item 8 (previously screened through #16 mesh screen) and item 9. Mix 15 minutes. |
| Step D: | Add item 16 (previously screened through #30 screen) to mix of Step C for 5 minutes. |
| Step E: | Compress in tablet press to the following specifications: |

Punch & Shape
13/32" FFB
Weight
10 tabs = 535 mg ± 10%
Thickness
0.185 ± 0.005"
Hardness
10–13 SCU
Friability
Less than 1%

Reasonable variations, such as those which would occur to a skilled artisan, can be made herein without departing from the scope of the invention.

What is claimed is:

1. A process for preparing tablets containing a foul tasting pharmaceutical agent in which the bad taste of the agent is effectively masked comprising the steps of:
   (a) wet-granulating a dry particulate pre-granulation blend comprising the agent and hydroxypropyl methylcellulose phthalate with an aqueous granulating composition in which said hydroxypropyl methylcellulose phthalate is at least partially soluble to form: a granulation containing the agent;
   (b) grinding and drying the product of step (a);
   (c) blending the product of step (b) with tablet adjuvants; and
   (d) compressing the product of step (c) to produce tablets.

2. The process of claim 1 wherein the agent is ibuprofen.

3. The process according to claim 2, wherein tablet adjuvants are blended with said ibuprofen containing granulation and the blend so formed is pressed into tablets.

4. The process according to claim 3, wherein the weight ratio of total tablet adjuvants is in the range of from about 2 parts to 3 parts to about 1 part of ibuprofen granulation.

5. The process according to claim 3, wherein the pH of said aqueous granulating composition is adjusted with an alkalizing agent or a buffering system so that it has a pH of about 5.5 or higher.

6. The process according to claim 5, wherein said pH is adjusted with an alkali metal citrate.

7. The process according to claim 5, wherein said pH is adjusted in the range of from about 5.5 to about 8.

8. The process according to claim 7, wherein said pH is adjusted with an alkali metal citrate.

9. The process according to claim 8, wherein
   (a) said ibuprofen comprises from about 30% to about 40% by weight of said pre-granulation blend based on the total weight of said pre-granulation blend;
   (b) said hydroxypropyl methylcellulose phthalate comprises from about 8% to about 10% by weight of said pre-granulation blend based on the total weight of said pre-granulation blend; and
   (c) said alkali metal citrate is present in said aqueous granulation composition at a concentration in the range of from about 60% to about 70% by weight based on the total weight of said aqueous granulating composition.

10. A process for preparing tablets containing a foul tasting pharmaceutical agent, in which the bad taste of the agent is effectively masked, comprising the steps of:
    (a) preparing an aqueous solution of buffering agent and sweetener;
    (b) preparing a dry blend of the pharmaceutical agent, a taste-masking agent and non-active adjuvants, admixing and granulating the product of step (a) therewith;
    (c) milling and drying the product of step (b);
    (d) tableting the mixture.

11. The process of claim 10 wherein the pharmaceutical agent is ibuprofen and the taste-masking agent is hydroxypropyl methylcellulose phthalate.

12. The process of claim 11 wherein the buffering agent is an alkali metal citrate.

13. The process of claim 12 wherein the buffering agent is potassium citrate.

* * * * *